United States Patent
Kunik et al.

(10) Patent No.: US 10,150,613 B2
(45) Date of Patent: Dec. 11, 2018

(54) PACKAGING DESIGNED TO BE A FUEL COMPONENT AND METHODS FOR MAKING AND USING SAME

(75) Inventors: Burton J. Kunik, Houston, TX (US); James C. Berns, Carthage, TX (US); David G. Gossman, Zwingle, IA (US)

(73) Assignee: Sharps Compliance, Inc., Houston, TX (US)

(*) Notice: Subject to any disclaimer, the term of this patent is extended or adjusted under 35 U.S.C. 154(b) by 995 days.

(21) Appl. No.: 13/476,731

(22) Filed: May 21, 2012
(Under 37 CFR 1.47)

(65) Prior Publication Data
US 2013/0081363 A1    Apr. 4, 2013

Related U.S. Application Data

(60) Provisional application No. 61/488,323, filed on May 20, 2011.

(51) Int. Cl.
| | |
|---|---|
| *B65B 1/04* | (2006.01) |
| *B65D 90/00* | (2006.01) |
| *F23G 5/44* | (2006.01) |
| *A61B 50/36* | (2016.01) |

(52) U.S. Cl.
CPC .............. *B65D 90/00* (2013.01); *A61B 50/36* (2016.02); *A61B 50/362* (2016.02); *B65B 1/04* (2013.01); *F23G 5/448* (2013.01); *F23G 2209/20* (2013.01)

(58) Field of Classification Search
CPC ........... B65B 1/04; B65D 90/00; F23G 5/448; F23G 2209/20; A61B 50/36; A61B 50/362

USPC ..................................................... 53/396, 395
See application file for complete search history.

(56) References Cited

U.S. PATENT DOCUMENTS

| | | | | | |
|---|---|---|---|---|---|
| 3,983,392 | A | * | 9/1976 | Armstrong ........... | G01N 23/203 378/88 |
| 4,136,624 | A | * | 1/1979 | Kato ...................... | F23G 5/002 110/236 |
| 4,240,363 | A | * | 12/1980 | Troy ...................... | B65D 29/02 110/241 |
| 4,886,164 | A | * | 12/1989 | Stein ...................... | A61B 50/36 206/366 |
| 4,978,028 | A | * | 12/1990 | George ......................... | 206/366 |
| 5,217,173 | A | * | 6/1993 | Koenig .................. | F23G 5/448 110/232 |
| 5,224,433 | A | * | 7/1993 | Benoit .................. | C04B 7/4407 110/226 |
| 5,356,022 | A | * | 10/1994 | Tipps ...................... | B65D 5/10 206/366 |
| 5,363,777 | A | * | 11/1994 | Yoshimoto .............. | F23G 5/165 110/214 |
| 5,890,443 | A | * | 4/1999 | Taya ........................ | A62D 3/40 110/346 |

(Continued)

*Primary Examiner* — Sameh Tawfik
(74) *Attorney, Agent, or Firm* — Robert W. Strozier

(57) ABSTRACT

Containers for disposal of waste materials, used or unused having desired burn properties. The containers have tailored or engineered properties based on material construction so that they are burnable and alter burn properties of the source materials, used or unused, contained therein. The containers may also include cavities into which accelerants, retarders, combustion aids, fuel value enhancing agents, additives to change an ash composition, other additives or the like are added.

13 Claims, 16 Drawing Sheets

(56) References Cited

U.S. PATENT DOCUMENTS

| | | | | |
|---|---|---|---|---|
| 5,928,618 | A * | 7/1999 | Maganas | B01D 53/83 |
| | | | | 358/1.15 |
| 6,087,548 | A * | 7/2000 | Levy | A61L 2/26 |
| | | | | 405/129.28 |
| 6,668,905 | B1 * | 12/2003 | Kadomura | B22D 18/02 |
| | | | | 164/97 |
| 7,823,576 | B2 * | 11/2010 | Timmons | C10L 5/368 |
| | | | | 126/25 B |
| 8,323,364 | B2 * | 12/2012 | Goble | B01J 7/02 |
| | | | | 423/644 |
| 8,496,044 | B2 * | 7/2013 | Seimiya | B21J 5/00 |
| | | | | 164/55.1 |
| 8,511,538 | B2 * | 8/2013 | Ouillette | B65D 5/46016 |
| | | | | 229/117.11 |
| 2011/0303666 | A1 * | 12/2011 | Kunik | A61B 19/026 |
| | | | | 220/200 |

* cited by examiner

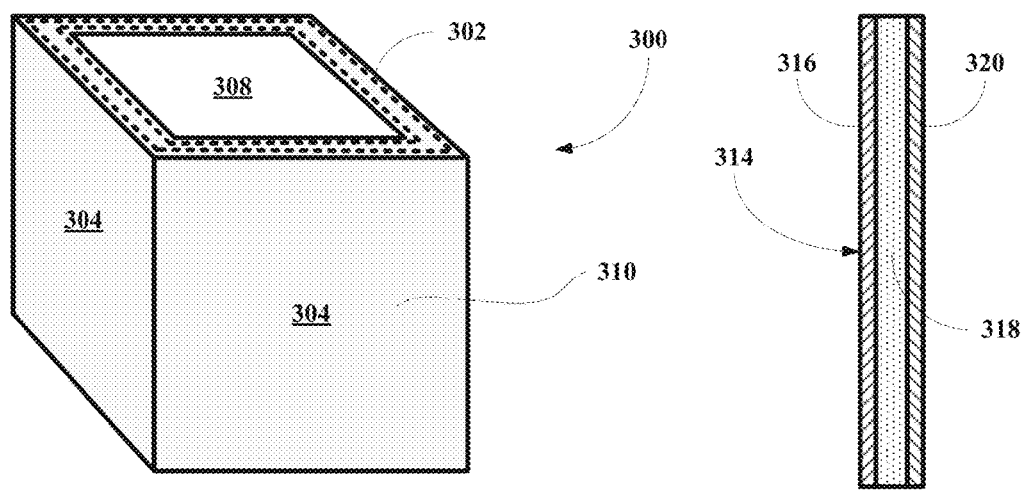
FIG. 3A  FIG. 3C
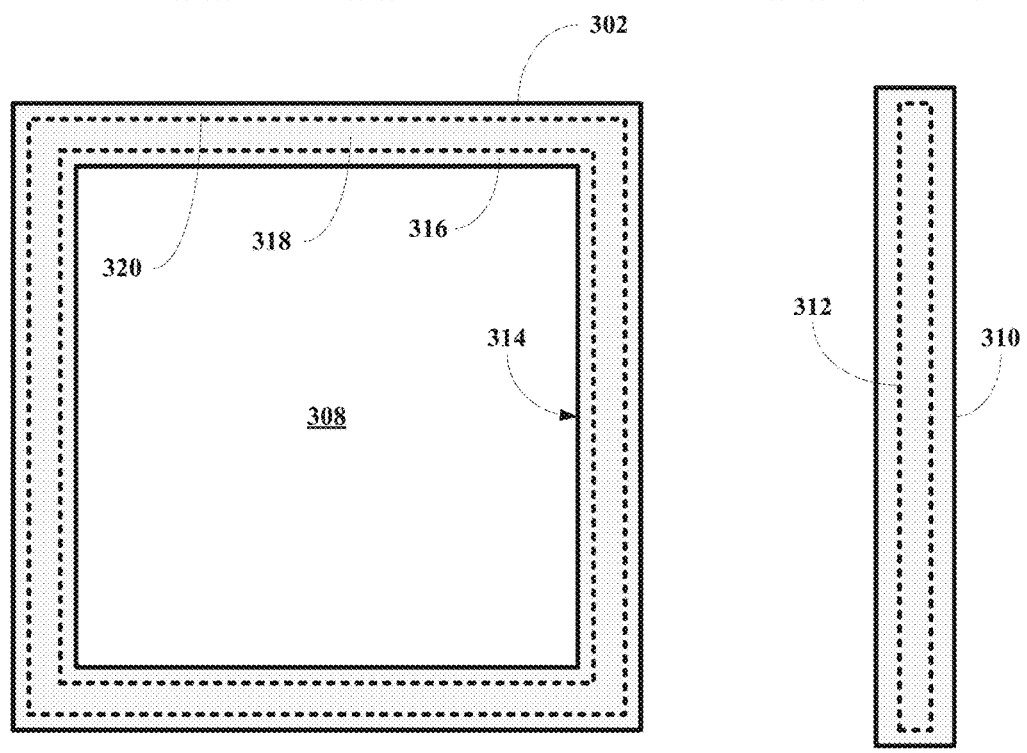
FIG. 3B  FIG. 3D

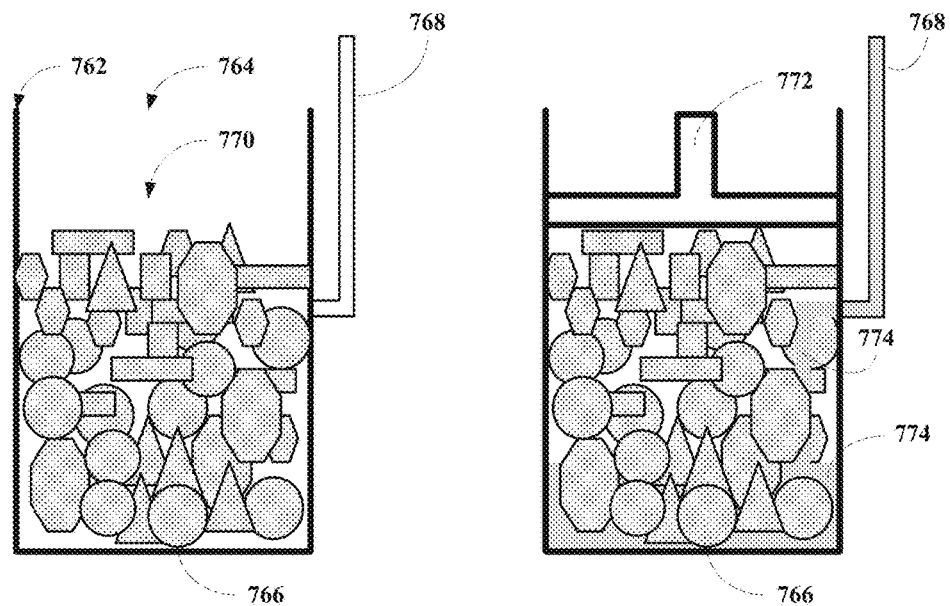
FIG. 7K     FIG. 7L
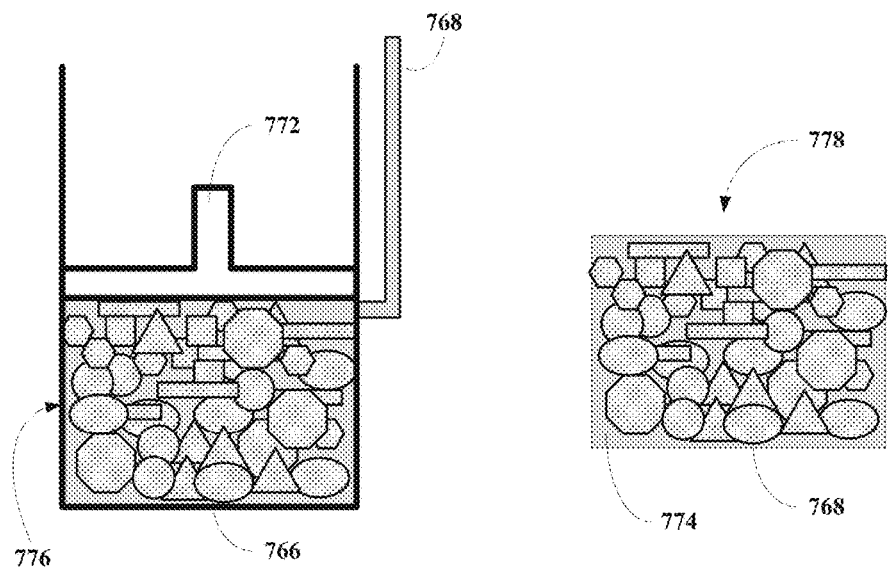
FIG. 7M     FIG. 7N

PACKAGING DESIGNED TO BE A FUEL COMPONENT AND METHODS FOR MAKING AND USING SAME

RELATED APPLICATIONS

The present application claims priority to and the benefit of U.S. Provisional Application Ser. No. 61/488,323, filed 20 May 2011 and is related to U.S. patent application Ser. No. 12/610,331 filed Nov. 1, 2009, now U.S. Pat. No. 8,100,989 issued Jan. 24, 2012 (24 Dec. 2012); Ser. No. 12/649,215 filed Dec. 29, 2009, now U.S. Pat. No. 8,163,045 issued Apr. 24, 2012; Ser. No. 12/649,230 filed Dec. 29, 2009, now U.S. Pat. No. 8,268,073 issued Sep. 18, 2012; Ser. No. 12/713,733 filed Feb. 26, 2010, and Ser. No. 12/814,251 filed Jun. 11, 2010, now U.S. Pat. No. 8,324,443 issued Dec. 4, 2012, incorporated by reference through the operation of the closing paragraph of the specification.

BACKGROUND OF THE INVENTION

1. Field of the Invention

Embodiments of the present invention relate to containers having desired combustion properties, where the container are designed for having source materials disposed therein for transport to a processing facility.

More particularly, embodiments of the present invention relate to containers for source materials, where the containers have desired combustion properties and/or alter combustion properties of source materials contained therein. In addition to the interior, the containers may also include other cavities into which accelerants, retardants, combustion aids, fuel value enhancing agents, additives to change a post-combustion ash composition, and/or other additives that alter the combustion properties of the container and/or the waste materials contained therein.

2. Description of the Related Art

Current packaging for source materials such as used and/or waste materials are not designed as a fuel component so that the container and the source materials contained therein can be effectively used as a fuel, with or without post-processing, in industrial processes and/or other processes.

Thus, there is a need in the art for containers for source materials, where the containers are designed to have engineered combustion properties, to alter combustion properties of source materials contained therein and/or to alter post combustion ash compositions of the filled containers.

SUMMARY OF THE INVENTION

Embodiments of this invention provide containers for source materials, where the containers are designed to have engineered combustion properties and/or to alter combustion properties of source materials contained therein. In certain embodiments, the containers are made of materials having engineered fuel values (amount of heat generated during combustion) and engineered resulting or post-combustion ash compositions. In other embodiments, the containers may be engineered to generate little or no ash. In other embodiments, the containers may be engineered to generate a specific post-combustion ash composition. In all embodiments, the containers, through a judicious selection of construction materials, may be engineered to have specific combustion properties such as a specific fuel value and/or a specific ash composition. Post-construction additives may be applied to, added to, and/or attached to the containers before or after filling with a source material to alter combustion properties of the container and the source material and/or an resulting ash composition after burning the container and the source material.

Embodiments of this invention also provide molded containers including a source material and a molding composition or a source material and a binding agent to form the molded containers, where the molded containers have desired combustion properties, where a compressing force is to is sufficient so that the molded container retains it shape during transportation and is between about 2 tons per square inch and about 2000 tons per square inch.

Embodiments of this invention provide containers for source materials, where the containers include a sealing coating adapted to isolate any hazardous or potentially hazardous materials contained therein. The types of hazardous or potentially hazardous materials that may be sealed by a sealing coating include new and/or used medical waste, used and/or new veterinary waste, and/or used and/or new healthcare waste, where the sealing coating may be a waterproof coating, a water resistant coating, an air or gas tight coating, an air or gas resistant coating, a solvent resistant coating, and/or other types of resistant coatings. The coating may comprise a single layer or multiple layers. The coatings are designed to either seal the container so that the container is water proof or water resistant, solvent resistant, air/gas tight, or to form a hermetically sealed container (gas and water tight). The coatings may also alter, modify and/or augment the fuel properties of the container on which the coatings are deposited.

Embodiments of this invention provide methods for preparing containers for source materials, where the containers are designed to have desired combustion properties and/or to alter, modify and/or augment the combustion properties of the source materials contained therein. The containers are constructed to include an interior for holding a desired volume of source materials, a means for depositing the source materials into the interior of the container, a means for closing the means for depositing, and, optionally, a means for sealing the container to form a sealed container well suited for transportation to a processing facility. The containers are constructed of one material or generally a plurality of materials so that the container are engineered to have specific combustion properties and post-combustion ash compositions, where these specific combustion properties altering, modifying and/or augmenting the combustion properties and/or post-combustion compositions of the source materials contained within the interior of the container, where the combustion properties are defined in greater detail herein.

Embodiments of this invention provide methods for using containers containing an amount of source material as a fuel, where the methods include depositing source materials into an interior of a container of this invention through an opening in the container to form a filled container, where the volume of the interior is sufficient to be filled with a desired volume of the source materials. Optionally, the methods also include forwarding the filled container to a processing facility, where the filled container may be processed to alter container combustion properties, source materials combustion properties, and/or an ash combustion of the filled container upon combustion. The methods also include forwarding the filled containers and/or the processed filled containers to a combustion facility, where the filled containers and/or the processed filled containers are used as a fuel in the combustion facility and where the combustion facility converts a portion of a fuel value of the filled containers and/or the processed filled containers into a useable form of energy or to use the heat and combustion ash to form a useable product.

BRIEF DESCRIPTION OF THE DRAWINGS

The invention may be better understood with reference to the following detailed description together with the appended illustrative drawings in which like elements are numbered the same:

FIGS. 3A-D depict a perspective view and a plan view of a rectangular solid container embodiment of this invention including a large rectangular opening and a lid, where the walls are of a composite construction.

DETAILED DESCRIPTION OF THE INVENTION

Figure 1A:
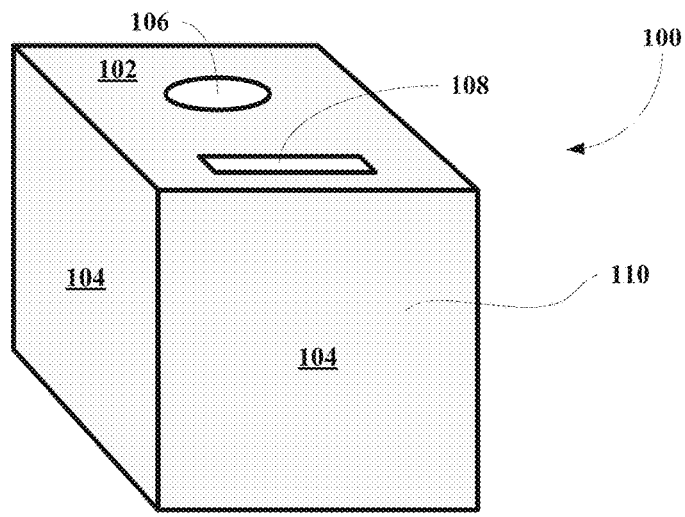
FIGS. 1A-C depict a perspective view and a top plan view of a rectangular container embodiment of this invention including a circular opening and rectangular opening and a lid or cover.

The inventors have found that containers for disposal of source materials can be constructed or constructed and post-processed to have specifically engineered combustion properties and/or a specifically engineered post-combustion ash compositions, where post-processing relates to augmenting the combustion properties of the containers after they are filled with a source material. The containers may include materials and/or components to alter or engineer specific combustion properties of the containers once filled with a source material or materials. The containers may exclude, eliminate or minimize materials and/or components that render the material unfit as a fuel or form an undesirable ash. The containers may also include materials and/or components that change the composition of the ash formed once the containers are burned. The containers may also be constructed or post-processed with materials, structures, and/or components to alter the combustion properties of the source materials contained therein or to alter the resulting ash composition derived from burning a filled container. The containers may also be processed prior to combustion to change the combustion properties of the container and/or the source materials contained therein and/or to change the resulting ash composition of the container and/or the source material contained therein. Thus, the inventors have found that containers may be constructed and/or post-processed to have a dual use: (1) a receptacle for receiving and transporting source materials, and (2) a fuel component along with the source material contained within the container. As a fuel, the containers and the source materials contained therein may significantly reduce landfill requirements for disposing of the filled containers.

Embodiments of this invention broadly relates to containers for source materials, where the containers have specifically engineered combustion properties. In certain embodiments, the engineered containers are constructed from materials having specific combustion properties and a specific post-combustion ash compositions. In other embodiments, the containers are engineered to be clean burning generating little or no ash. In other embodiments, the containers are engineered to generate an engineered ash composition upon combustion. In all embodiments, the containers, through a judicious selection of materials, may be engineered to have specific combustion properties, such as specific fuel value regardless of a composition of the post-combustion ash and vis-a-versa. Post-processing of the filled containers may result in specific alterations of one or more the combustion properties of the filled containers. The containers may also include coatings, liners, inserts, or other components that change, alter, modify and/or augment the combustion properties or resulting ash compositions of the containers and/or of the source materials within the containers. Embodiments of this invention also relate to molded containers for source materials including a source material or plurality of source materials and a molding composition to form the molded containers, where the molded containers have desired combustion properties and/or post-combustion ash compositions.

Embodiments of this invention broadly relate to methods for using containers for depositing source materials, where the containers have desired properties. The containers are constructed to include an interior, a means for depositing source materials into the interior of the container, and a means for closing and/or sealing the means for depositing. The means for depositing may be an opening, an aperture, an openable aperture, and/or any other means for depositing new and/or used source materials into the interior of the container. The means for closing and/or sealing the means for depositing may be a lid, a slidable closing member, a top, a cover, and/or any other closing and/or sealing means. The methods may also include depositing source materials into the interior of the container. The methods may also include sealing the container and sending the container for combustion or post-processing and combustion.

In certain embodiments, the containers may be constructed to be devoid of most metals and inorganic constituents. These containers would find application in power plants or other uses where ash is to be minimized. In other embodiments, certain metals, metal oxides or other inorganic constituents may be of use in the ultimate process using the containers and their contents as fuel. Examples of metals, metal oxides, or other inorganic constituents included, without limitation, silicon, silica, calcium containing compounds, aluminum, aluminum containing compounds, iron, iron alloys, and iron containing compounds or other inorganic constituents that may yield a desired post-combustion ash composition or mixtures or combinations thereof. One such process occurs in cement plants, where such ingredients are necessary for the production of a clinker composition or a cement composition, and may therefore be a beneficial addition to the fuel mix.

In other embodiments, the containers are constructed to use specific water absorbing agents, specific moisture absorbing agents and/or specific drying agents. Drying agents or moisture absorbing agents are often added to containers to maintain the contents deposited into the container at a desired dryness. If the containers are to find application as a fuel component in cement plants, then the drying agent may be metal oxides or metal salt drying agents that would be useful in a cement kiln. If instead the desire is to minimize ash upon combustion of the containers such as for use in power plants or other applications that require minimal ash production, then the containers may include water absorbing polymeric materials such as hydrogels, ionomers, polyacrylates, polyacrylamides or other similar water absorbing polymeric materials. Alternatively, the container may be constructed to include removable drying pouches.

In certain embodiments, the containers may be constructed to be prevent metal cans, fasteners, and/or glass containers from being deposited therein.

In other embodiments, the container may be constructed to be substantially or completely devoid of polyvinyl chloride or other polymers that produce undesirable effluents during combustion, especially for use in clean burn facility such as power plants.

In other embodiments, the containers of this invention comprise source materials encased in a burnable matrix and/or compacted and encased in a burnable matrix. The containers may result from the encasing or the encasing material may be injected into an interior of a container filled with a source material.

In other embodiments, the containers of this invention, once filled and returned, may be have a composition injected into the interior of the container, sprayed onto to the exterior of the container, inserted into pockets in the container, attached to the container, or mixtures or combinations of these post-receipt processes, where the post-receipt processes are designed or adapted to alter, modify, and/or augment combustion properties and/or resulting ash compositions of the containers and the contents therein.

The containers of the present invention may be of any desired shape including, without limitation, a polygonal solid such as a rectangular solid such as a box, a cylinder such as a barrel, a sphere, an ellipsoidal solid, a trapezoidal solid, or any other solid shaped container or combinations thereof.

In certain embodiments, the containers may include sides made of composites such as layer of a paper material and a polymer material. The containers may also be designed to be coated, sprayed, dipped, wrapped, or otherwise partially or completely surrounded by a fuel value augmenting material or coating material or an ash composition augmenting material or coating material. The containers may also be constructed with liners, where the liners have combustion properties that are the same or different from the construction of the walls of the containers. The containers may also to include a separate receptacle disposed within the interior or the container, where the receptacle contains the source material and the receptacle have the same or different combustion properties from the walls of the containers. The container may also include inserts that may be placed inside groove in the container walls, where the inserts have combustion properties that are the same or different from the construction of the walls of the containers. The design of container including additional layers, liners, and/or inserts serves a dual propose: 1) they improve container integrity, safety, and/or security and 2) type alter, optimize and/or augment combustion properties.

Suitable Reagents and Equipment of the Invention

Suitable means for depositing include, without limitation, openings, apertures, openable apertures, slidable members, hook-and-loop activated openings, magnetically activated openings, other means for depositing materials into the interior of a container or mixtures or combinations thereof.

Suitable means for closing include, without limitation, lids, tops, covers, slidable members, hook-and-loop activated openings, magnetically activated closings, other closing member and devices, or mixtures or combinations thereof.

Suitable slots, apertures or openings include, without limitation, any shaped slot, opening or aperture. The shapes include, without limitation, circular, ellipsoidal, polygonal such as a triangular slot, a square slot, rectangular slot, a hexagonal slot, etc., or any other slot shape or combinations thereof.

Suitable means for sealing include, without limitation, sealing lids, sealing tops, sealing covers, other sealing members or devices, or mixtures or combinations thereof.

Suitable combustion properties include, without limitation, fuel value, rate of combustion, resulting ash composition, ignition temperature, lowest ignition temperature, highest ignition temperature, average ignition temperature, accelerant content, oxygen content, halogen content, retarder content, inorganic content, container shape, distribution of fuel components, other properties affecting combustion, or mixtures or combinations thereof.

Suitable metal oxide and ceramic drying agents include, without limitation, silicas such as silica gel, aluminas, aluminosilicates, silicoaluminates, molecular sieves, other metal oxide drying agents, other ceramic drying agents, or mixtures or combinations thereof.

Suitable materials out of which the container may be constructed include, without limitation, plastics, rubbers, metals, woods, ceramics, composites, oxidizing agents, or mixtures or combinations thereof. In certain embodiments, the materials include non-halogenated plastics. In other embodiments, the materials include cardboard and wax coated cardboard that have a good fuel value and is often itself derived from secondary wood fiber sources. In certain embodiments, the container of this invention may also include plastic bags disposed in the interior or liners. The bags and/or liners may be of a type that will alter the fuel value of the containers and/or the source material contained in the container.

Suitable source materials include, without limitation, any used or waste material. Exemplary examples of used or waste materials include, without limitation, used or waste industrial materials, used or waste municipal materials, used or waste healthcare materials, used or waste medical materials, used or waste agricultural materials, used or waste biomass materials, used or waste electronic materials, used or waste metal materials, or mixtures or combinations thereof. Used or waste healthcare and used or waste medical waste may include medical waste, generated by people, doctors, doctor offices, clinics, emergency clinics, hospitals, dentists, dentistry clinics and hospitals, veterinarians, veterinary clinics and hospitals, farms, farmer, ranches, ranchers, or producers of used or waste material and/or other facilities that produce used or waste material. These used or waste materials are generally complex mixtures of components including, without limitation, pulp materials, fiber materials, fabric materials, polymer materials, metal materials, ceramic materials, ash materials, other materials and/or mixtures or combinations thereof.

Pulp materials suitable for use herein include, without limitation, wood, wood chips, sawdust, paper, cardboard, and/or mixtures or combinations thereof.

Fiber materials suitable for use herein include, without limitation, natural fibers, synthetic fibers, or the like and mixtures or combinations thereof. Exemplary fibers include, without limitation, inorganic fibers, carbon fibers, boron-nitride fibers, organic fibers, ceramic fibers, glass fibers, any other fibrous material and mixtures or combinations thereof.

Fabric materials suitable for use herein include, without limitation, any natural or synthetic fabric and mixtures or combinations thereof. Exemplary examples include, without limitation, cotton, wool and other fabrics made from animals or plants, RAYON, DACRON, fabric made of polyamides, or any other fabric or mixtures or combinations thereof.

The metal or metallic materials include, without limitation, any metal or metal alloy including a metal from the periodic table of elements. Exemplary examples include, alkali metals (Group 1 metals), alkaline earth metals (Group 2 metals), transition metals (Group 3-12 metals), Lanthanide metals, Actinide metals, post-transition metals, metalloids, or mixtures or combinations thereof. Certain metals and metalloids may be removed prior to use depending on the use to which the burnable fuels is put. The metals may be in any form include fibers, pieces, devices including metals, etc. and mixtures or combinations thereof. Exemplary examples include waste electronic devices. Of course, it should be recognized to one of ordinary skill in the art, that certain metals and metal alloys either pose a health or environmental concerns or issue or process concern or issues. Exemplary examples of such metals or metal alloys would include mercury, cadmium, lead, and thallium and radioactive elements and/or isotopes.

Ceramic materials suitable for use herein include, without limitation, any ceramic material or ceramic containing material or mixtures or combinations thereof. Exemplary examples include, without limitation, electronic substrates, glass, dishes, clay pots, any other object that contains a ceramic material, and mixtures or combinations thereof.

The polymer materials suitable for use herein include, without limitation, plastics, thermoplastics, elastomers, thermoplastic elastomers, resins, and other polymer or polymeric materials and/or mixtures or combinations thereof. In certain embodiments, the polymer materials used in the construction of the container are free or substantially free of chlorine, lead, arsenic or other hazardous components, where substantially means the container should generate less than 500 ppm of these components. In other embodiments, the amount should be less than 250 ppm. In other embodiments, the amount should be less than 100 ppm. In other embodiments, the amount should be less than 50 ppm. In other embodiments, the amount should be less than 25 ppm. In other embodiments, the amount should be less than 10 ppm. In other embodiments, the amount should be less than 1 ppm. In other embodiments, the amount should be less than 500 ppb. In other embodiments, the amount should be less than 250 ppb. In other embodiments, the amount should be less than 100 ppb. In other embodiments, the amount should be less than 50 ppb.

Agricultural materials suitable for use herein include, without limitation, any agricultural waste, any agricultural packaging material and mixtures or combinations thereof.

Biomass materials suitable for use herein include, without limitation, any plant matter that is left over after processing to produce an end product such as sugar cane and sugar beet processing, and mixtures or combination thereof.

Other materials may include, without limitation, chemicals, ash, pharmaceuticals (e.g., unused pharmaceuticals, expired pharmaceuticals, or any other pharmaceutical compositions), ceramics, binding agents, composites materials of one or more of the components set forth above, any other materials and/or mixtures or combinations thereof. The inventors have also found that ash derived from incinerating certain used or waste materials, where the ash still has material or fuel value may be added to the material to change or augment a compositional makeup of the fuel.

In all of the mixtures, polymer materials from other sources of waste, unused and/or virgin polymer materials may be added as binding agents to the material before burning or before forming the material into a desired compact shape followed by combustion of the fuel. The inventors believe that polymer materials act as binders in the shaping process, e.g., pelletizing, and help to increase the combustible nature of the resulting fuel.

The used or waste material may include any mixture or combination of any of the above identified materials.

Suitable virgin and/or unused materials may be any material that has not been used and is added to the input material to change a property of the resulting fuel including altering a fuel value of the material, altering an ash composition of the material, expired pharmaceuticals, altering a fluidity of the material, altering a bulk density of the material, altering the cohesiveness of the material, altering the wettability of the material, or altering other properties or two or more properties of the material or mixtures or combinations thereof.

Suitable coating materials include, without limitation, oils (synthetic oils or natural animal or plant oils), medium to high melting point hydrocarbons, waxes, oligomers, low molecular weight polymers, high molecular weight polymers, resins, thermosetting resins, thermoplastics, elastomers, photo-curable monomers, thermally curable monomers, curable monomers, polymerizable monomers, photo-curable oligomers, thermally curable oligomers, polymerizable oligomers, photo-curable polymers, thermally curable polymers, polymerizable polymers, other materials that may form a desired coating or particle coating on the particulate fuels of this invention or mixture or combinations thereof. The coatings are designed to augment, adjust, change or alter one or more characteristics of the particulate fuel. The coatings may include water proofing coatings, water resistant coatings and/or solvent resistant coatings. These coatings may include, without limitation, polyesters such as MYLAR®, polyolefins, fluorinated polymers, epoxy resins, phenolic resins, acrylates, waxes, latices, neoprene or other chlorinated polymers (provided that the chlorine does not exceed requirements of the facility designed to utilize the container), or mixtures or combinations thereof.

DETAILED DESCRIPTION OF THE DRAWINGS

Figure 1B:
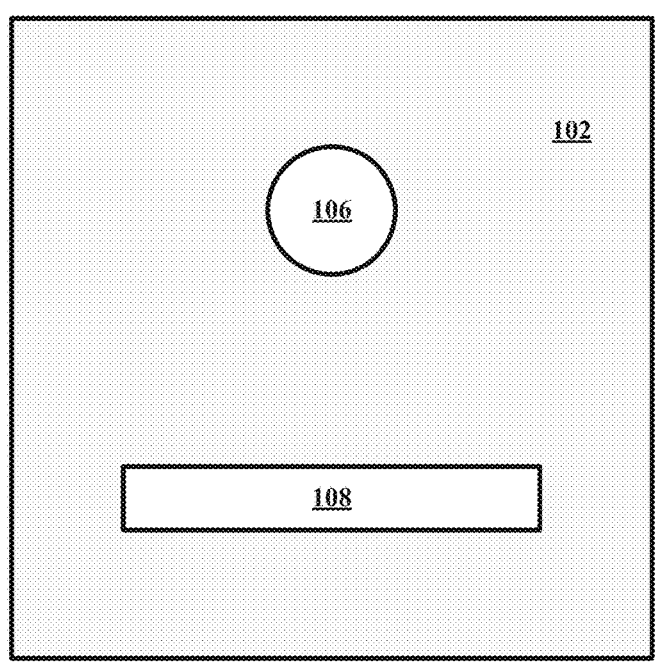
Figure 1C:
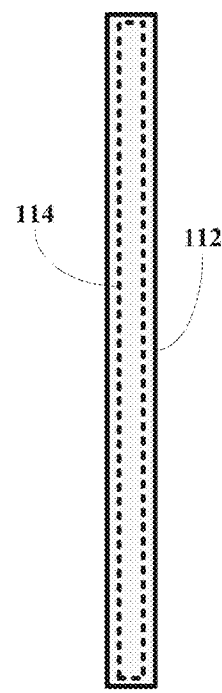

Referring now to FIGS. 1A-C, an embodiment of a hollow rectangular solid container or box, generally 100, is shown to include a top 102 and five sides 104 (two shown here). The top 102 includes a circular opening 106 and a rectangular opening 108 allowing access to an interior 110 of the box 100. The container or box 100 also includes a lid or cover 112 designed to fit over the top 102 of the box 100 closing access to the openings 106 and 108. The lid 112 is also adapted to facilitate transportation of the box 100 to a processing facility. Interior surfaces of the lid 112 may include protected adhesive strips 114 so that the lid 112 will adhesively seal or bond to the sides 104 of the box 100. The box 100 may be constructed out of cardboard, a polymer material such as a plastic material, plastic reinforced cardboard, coated cardboard, or mixtures or combinations thereof and may include organic or inorganic drying agents disposed in the interior 110 of the box 100.

Figure 1D:
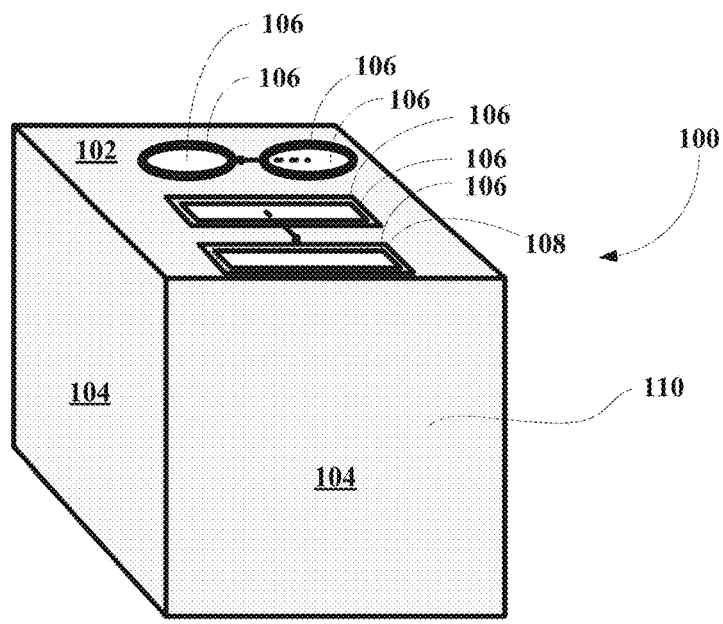
FIGS. 1D&E depict a perspective view and a top plan view of another rectangular container embodiment of this invention including a circular opening, a rectangular opening, adhesive patches and attached lids.
Figure 1E:
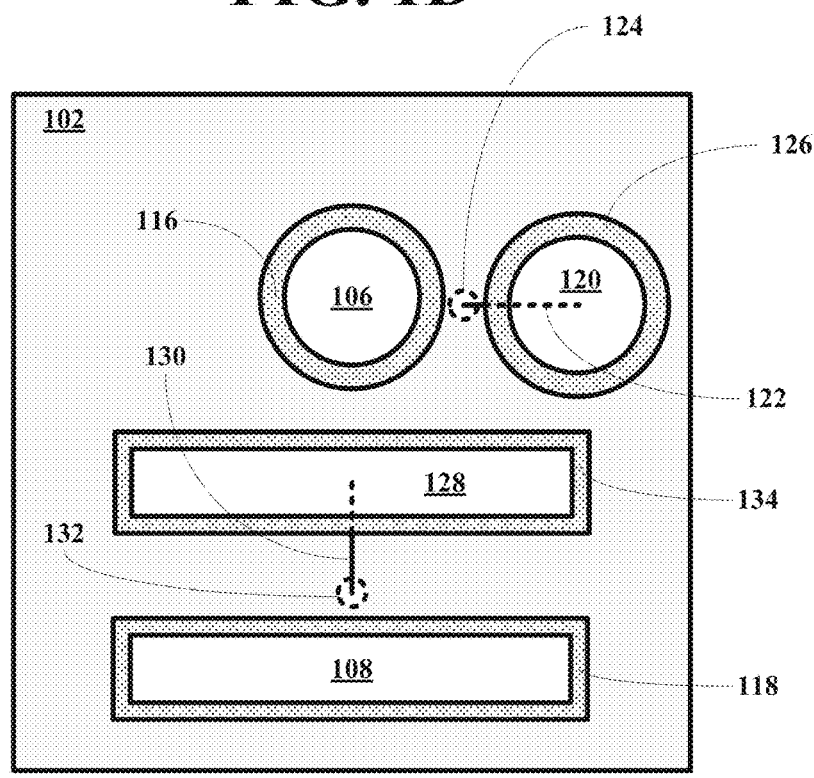
FIGS. 1F-I depict a perspective view and a top plan view of another rectangular container embodiment of this invention including a circular opening and rectangular opening, along with perspective view of a circular lid and a rectangular lid.
FIGS. 1J&K depict a perspective view and a top plan view of another rectangular container embodiment of this invention including a circular opening and rectangular opening, both having slidable lids.
Figure 1F:
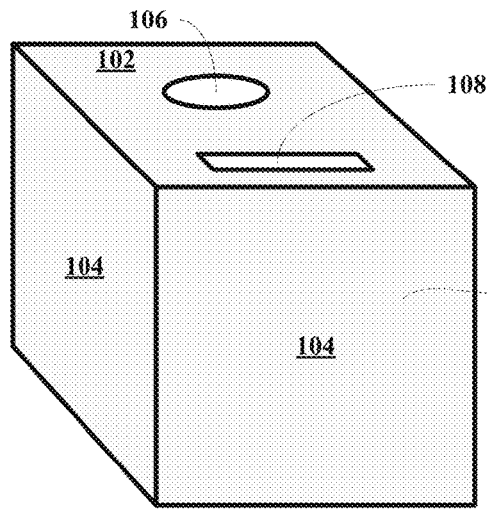
Figure 1H:
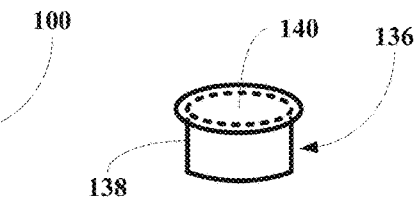
Figure 1I:
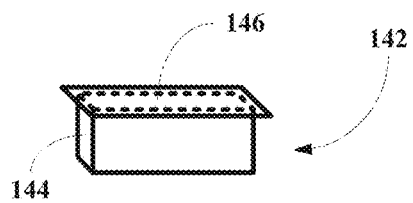
Figure 1G:
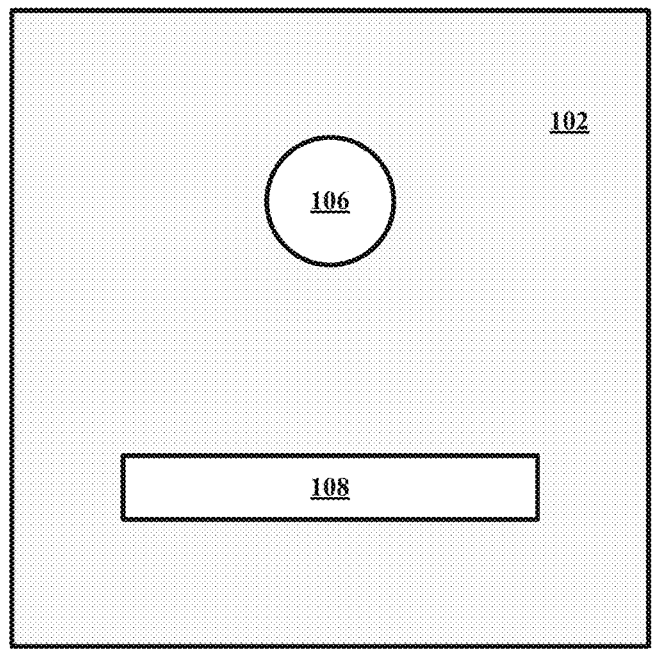

Referring now to FIGS. 1D-E, an embodiment of a hollow rectangular solid container or box, generally 100, is shown to include a top 102 and five sides 104 (two shown here). The top 102 may include a circular opening 106 and/or a rectangular opening 108 allowing access to an interior 110 of the box 100. The box 100 also includes a first adhesive ring 116 surrounding the circular opening 106 and a rectangular adhesive strip 118 surrounding the rectangular opening 108. The first adhesive ring 116 is covered with a ring shaped release sheet (not shown), and the rectangular adhesive strip 116 is covered with a rectangular release sheet (not shown). The box 100 also includes a circular sealing member 120 attached to the box 100 by a flexible member 122 anchored to a first retaining tab 124 disposed on an inner surface of the top 102 and to the top surface of the member 120, where the circular sealing member 120 includes a second adhesive ring 126 covered by a release sheet (not shown). The box 100 may include both adhesive rings 116 and 126 or just one depending on design criteria. The box 100 may also include a rectangular sealing member 128 attached to the box 100 by a second flexible member 130 anchored to a second retaining tab 132 and to the top surface of the member 128, where the rectangular sealing member 128 includes a second rectangular adhesive strip 134 covered by a release sheet (not shown). The box 100 may include both adhesive strips 118 and 134 or just one depending on design criteria. The box 100 may be constructed out of cardboard, a polymer material such as a plastic material, plastic reinforced cardboard, coated cardboard, or mixtures or combinations thereof and may include organic or inorganic drying agents disposed in the interior 110 of the box 100.

Referring now to FIGS. 1F-I, an embodiment of a hollow rectangular solid container or box, generally 100, is shown to include a top 102 and five sides 104 (two shown here). The top 102 includes a circular opening 106 and a rectangular opening 108 allowing access to an interior 110 of the box 100. The container or box 100 also includes a circular lid 136 having a cylindrical member 138 extending downward from a top 140. The cylindrical member 138 is designed to fit into the circular opening 106. The box 100 also includes a rectangular lid 142 having an insertion member 144 extending downward from a top 146. The insertion member 144 is designed to fit into the rectangular opening 108. The two lids 136 and 142 are inserted into their respective openings 106 and 108 after the box is filled, but prior to shipment to a processing facility. The box 100 may be constructed out of cardboard, a polymer material such as a plastic material, plastic reinforced cardboard, coated cardboard, or mixtures or combinations thereof and may include organic or inorganic drying agents disposed in the interior 110 of the box 100.

Figure 1J:
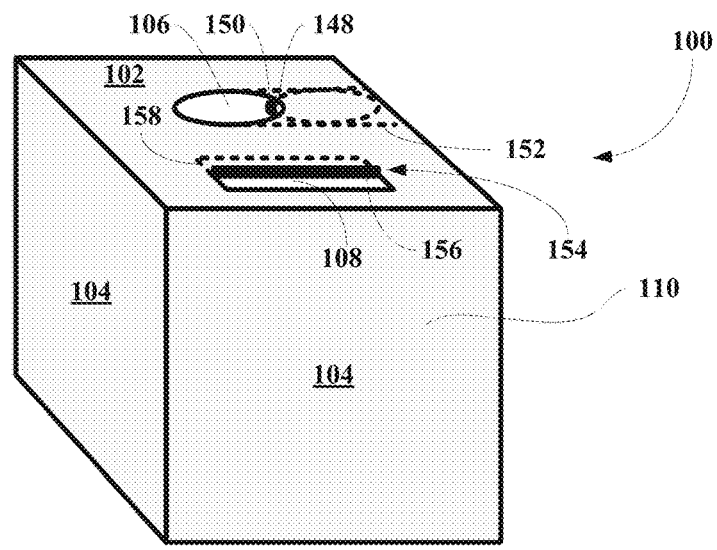
Figure 1K:
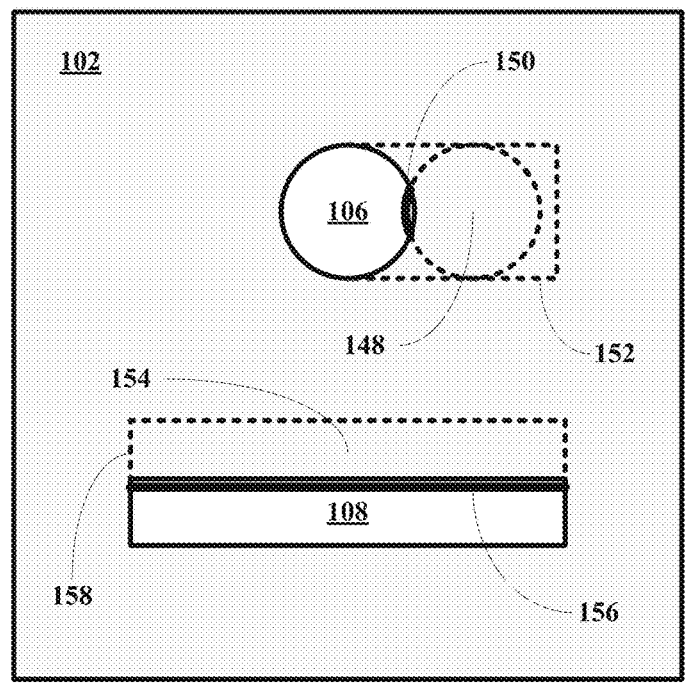

Referring now to FIGS. 1J-K, an embodiment of a hollow rectangular solid container or box, generally 100, is shown to include a top 102 and five sides 104 (two shown here). The top 102 includes a circular opening 106 and a rectangular opening 108 allowing access to an interior 110 of the box 100. The box 100 also includes a slidable circular closing member 148 including an upward extending member 150, where the member 148 is mounted in a first slot 152 in the top 102. The member 150 is adapted to permit the member 148 to transition between its opened position and its closed position by sliding the member 148 to the left or to the right. The box 100 also includes a slidable rectangular closing member 154 including an upward extending member 156, where the member 154 is mounted in a second slot 158 in the top 102. The member 156 is adapted to permit the member 145 to transition between its opened position and its closed position by sliding the member 154 up or down. The box 100 may be constructed out of cardboard, a polymer material such as a plastic material, plastic reinforced cardboard, coated cardboard, or mixtures or combinations thereof and may include organic or inorganic drying agents disposed in the interior 110 of the box 100.

Figure 2A:
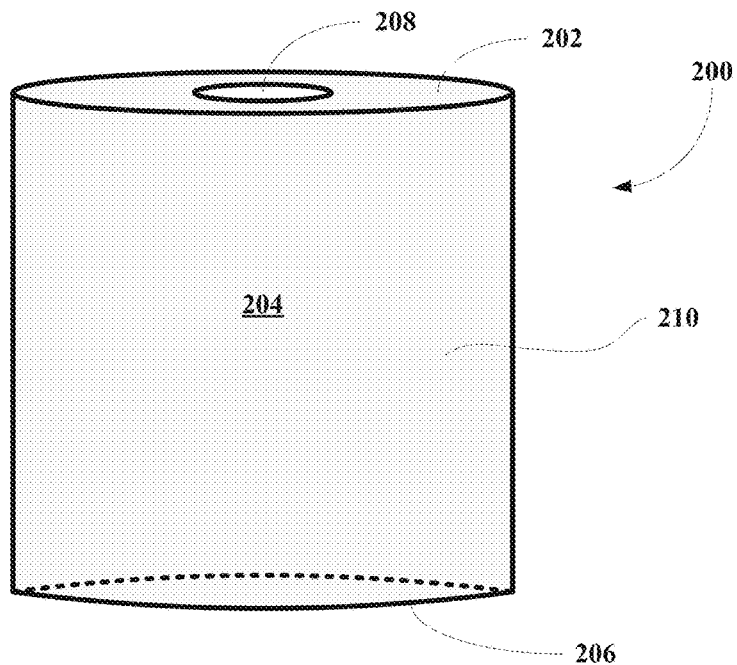
FIGS. 2A-C depict a perspective view and a plan view of a cylindrical container embodiment of this invention including a circular opening and a lid.
Figure 2B:
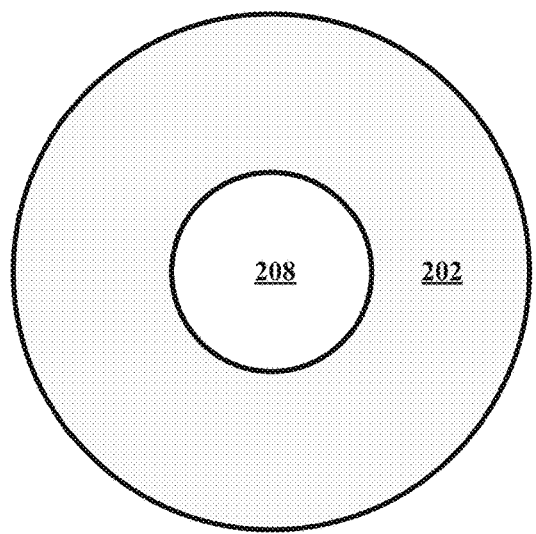
Figure 2C:
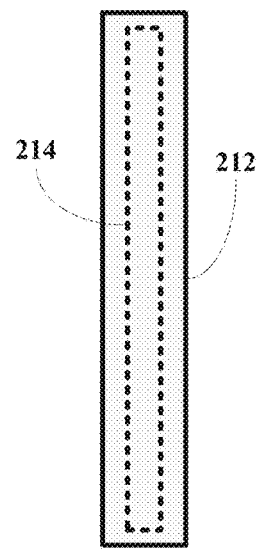
Figure 4A:
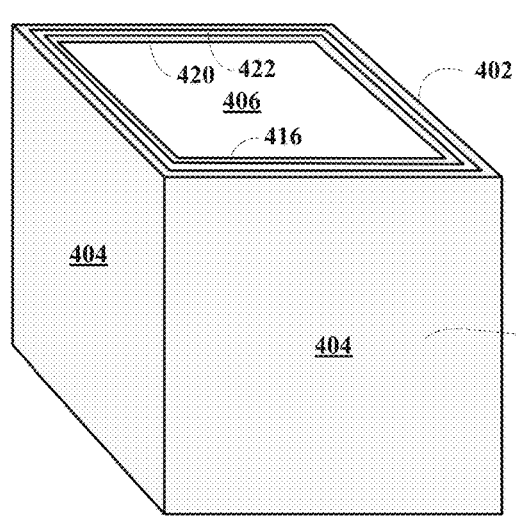
FIGS. 4A-D depict a perspective view and a plan view of a rectangular solid container embodiment of this invention including a large rectangular opening and a lid, where the walls are slotted.
Figure 4C:
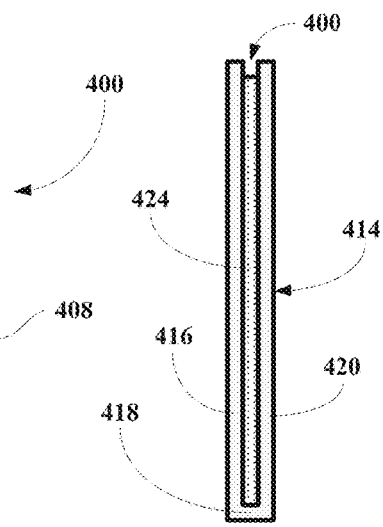
Figure 4B:
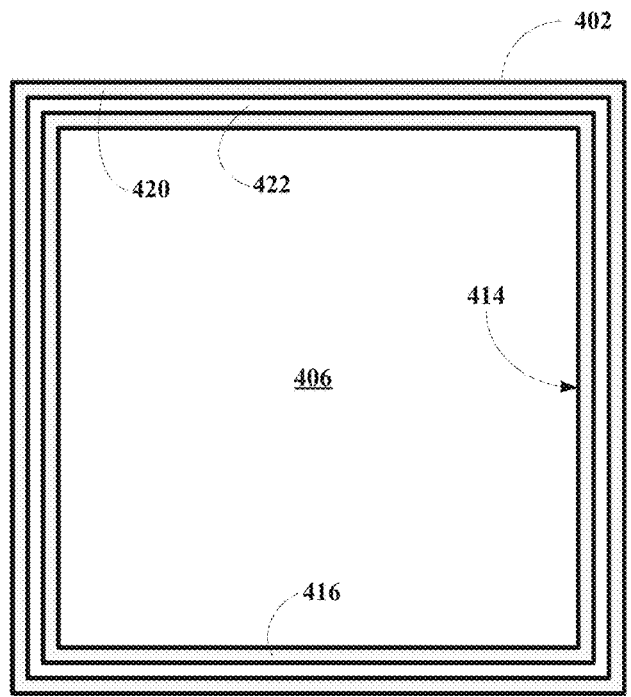
Figure 4D:
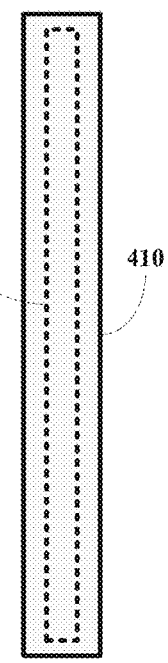
Figure 5A:
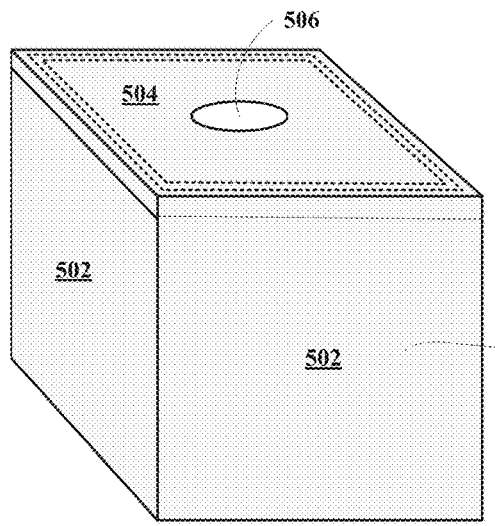
FIGS. 5A-D depict a perspective view and a plan view of a rectangular solid container embodiment of this invention including a circular opening and a lid, where the container includes a liner.
Figure 5C:
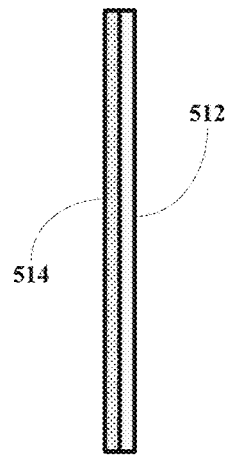
Figure 5B:
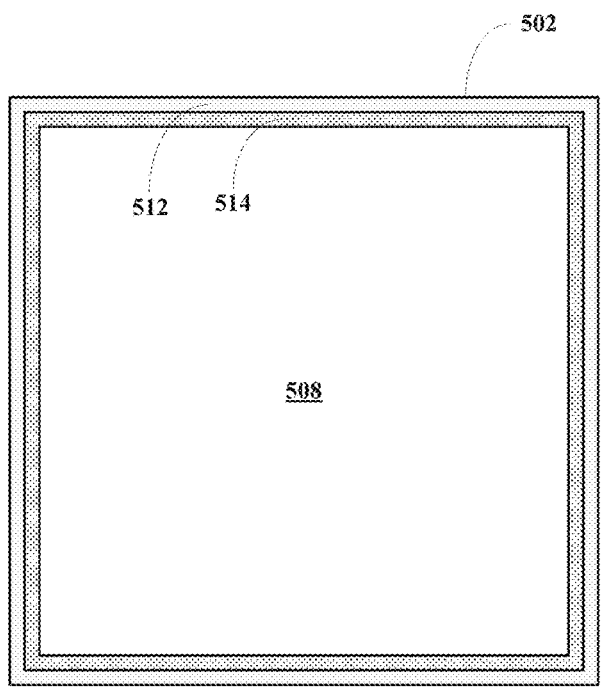
Figure 5D:
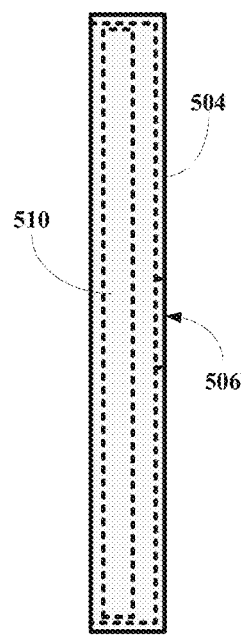

Referring now to FIGS. 2A-C, an embodiment of a barrel type container, generally 200, is shown to include a top 202, a cylindrical side 204, and a bottom 206 (two shown here). The top 202 includes a circular opening 208 allowing access to an interior 210 of the box 200. The container 200 also includes a lid or cover 212 designed to fit over the top 202 of the container 200 closing access to the opening 208. The lid 212 is also adapted to facilitate transportation of the container 200 to a processing facility. Interior surfaces of the lid 212 may include protected adhesive strips 214 so that the lid 212 will adhesively seal or bond to the side 204 of the container 200. The box 200 may be constructed out of cardboard, a polymer material such as a plastic material, plastic reinforced cardboard, coated cardboard, or mixtures or combinations thereof and may include organic or inorganic drying agents disposed in the interior 210 of the box 200.

Referring now to FIGS. 3A-D, an embodiment of a hollow rectangular solid container or box, generally 300, is shown to include a top 302 and five sides 304 (two shown here). The top 302 includes a rectangular opening 306 allowing access to an interior 308 of the box 300. The container or box 300 also includes a lid or cover 310 designed to fit over the top 302 of the box 300 closing access to the opening 306. The lid 310 is also adapted to facilitate transportation of the box 300 to a processing facility. Interior surfaces of the lid 310 may include protected adhesive strips 312 so that the lid 310 will adhesively seal or bond to the sides 304 of the box 300. The walls 304 comprise a composite structure 314 including an inner layer 316, a middle layer 318 and an outer layer 320. The layers 316, 318 and 320 may be made of the same or different material and are chosen to impart desired combustion properties to the container 300. In certain embodiments, the inner layer 316 is a plastic material, the middle layer 318 is a fuel augmenting material and the outer layer 320 is cardboard. In other embodiments, the inner and outer layers 316 and 320 are cardboard and the middle layer 318 is a plastic material. In other embodiments, the inner and outer layers 316 and 320 are cardboard or a plastic material and the middle layer 318 is an ash modifying material. In other embodiments, the inner and outer layers 316 and 320 are cardboard or a plastic material and the middle layer 318 is a metal or metal oxide modifying material, where the metal or metal oxide alters, modifies and/or augments the post-combustion ash composition of the container 300.

Referring now to FIGS. 4A-D, an embodiment of a hollow rectangular solid container or box, generally 400, is shown to include a top 402 and five sides 404 (two shown here). The top 402 includes a rectangular opening 406 allowing access to an interior 408 of the box 400. The box 400 also includes a lid or cover 410 designed to fit over the top 402 of the box 400 closing access to the opening 406. The lid 410 is also adapted to facilitate transportation of the box 400 to a processing facility. Interior surfaces of the lid 410 may include protected adhesive strips 412 so that the lid 410 will adhesively seal or bond to the sides 404 of the box 400. The walls 404 comprise a slotted structure 414 including an inner wall 416, a bottom wall 418 and an outer wall 420. The walls 416, 418, and 420 form a slot 422. The slot 422 is adapted to receive an insert 424. The walls 416, 418, and 420 and the insert 424 may be made of the same or different material and are chosen to impart desired combustion properties and/or desired post-combustion ash properties to the container 400. In certain embodiments, the walls 416, 418, and 420 are cardboard and the insert 424 is a polymer material. In other embodiments, the walls 416, 418, and 420 are a polymer material and the insert is cardboard or a different polymer material. In other embodiments, the walls 416, 418, and 420 are cardboard are cardboard or a plastic material and the insert 424 is an ash modifying material. Alternatively, the slot 422 may be divided into a plurality of pockets so that different material may be added to the container 400 during or after construction.

Referring now to FIGS. 5A-D, an embodiment of a hollow rectangular solid container, generally 500, is shown to include five sides 502 (two shown here). The container 500 also include a lid 504 includes a circular opening 506. The container 500 also includes an interior 508 into which source material is deposited through the opening 506. The opening 506 may be closed using any of the closing members shown in FIGS. 1D-K. The lid 504 and closing member are also adapted to facilitate transportation of the container 500 to a processing facility. Interior surfaces of the lid 504 may include protected adhesive strips 510 so that the lid 504 will adhesively seal or bond to the sides 502 of the container 500. The sides 502 are constructed of a container layer 512 and a liner 514. The container layer 512 may be constructed of cardboard, a polymer material such as a plastic material, plastic reinforced cardboard, coated cardboard, or mixtures or combinations thereof and may include organic or inorganic drying agents disposed in the interior 508 of the container 500. The liner 514 may be constructed of the same materials as the container, but in most embodiments, the liner 514 will be a polymer material.

Figure 6A:
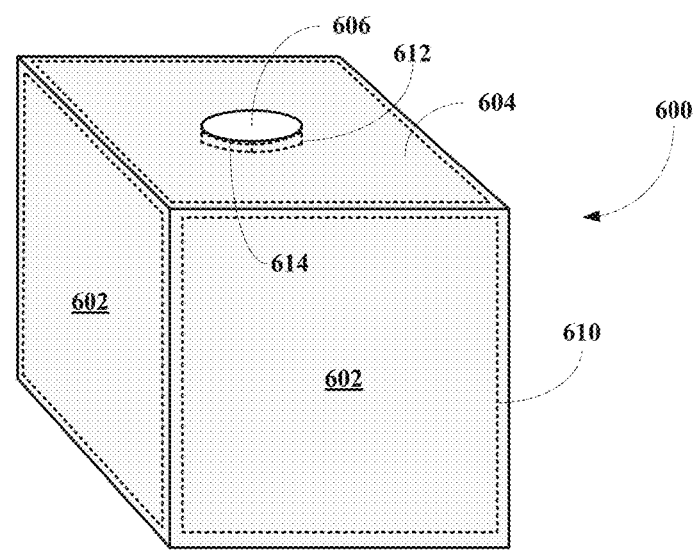
FIGS. 6A-C depict a perspective view and a plan view of a rectangular solid container embodiment of this invention including a circular opening and a lid, where the container includes receptacle.
Figure 6B:
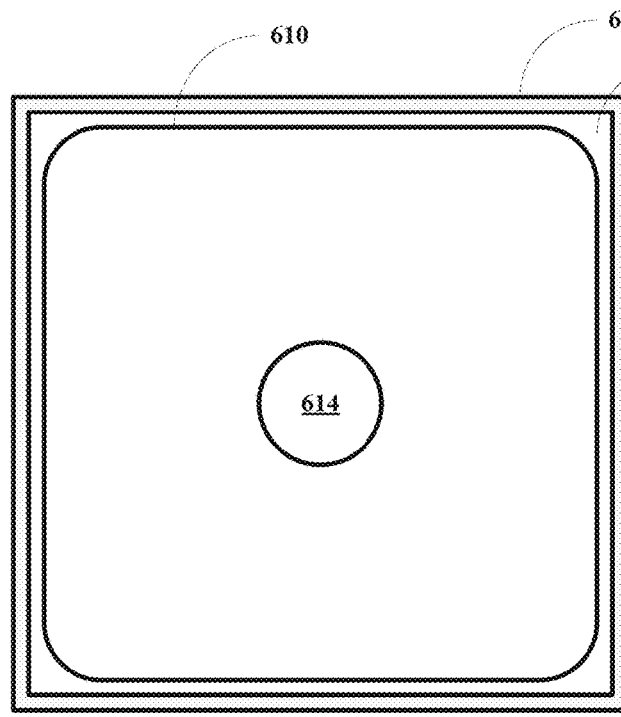
Figure 6C:
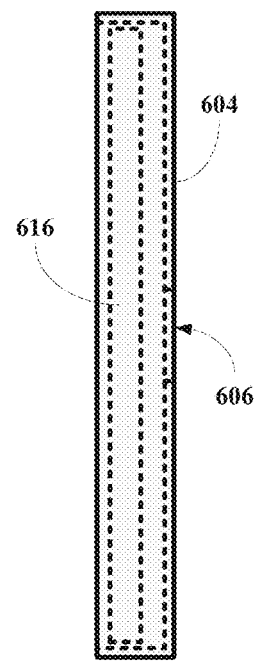

Referring now to FIGS. 6A-C, an embodiment of a hollow rectangular solid container, generally 600, is shown to include five sides 602 (two shown here). The container 600 also include a lid 604 includes a circular opening 606. The container 600 also includes an interior 608 having disposed therein a receptacle 610 having a neck 612 and a circular opening 614 so that the lid opening 606 aligns with the receptacle opening 614. Interior surfaces of the lid 604 may include protected adhesive strips 616 so that the lid 604 will adhesively seal or bond to the sides 602 of the container 600. The container 600 may be constructed out of cardboard, a polymer material such as a plastic material, plastic reinforced cardboard, coated cardboard, or mixtures or combinations thereof and may include organic or inorganic drying agents disposed in the interior 608 of the container 600. The receptacle 610 may be constructed of the same materials as the container, but in most embodiments, the receptacle 610 will be structured of a polymer material. Source materials are deposited into the receptacle 610. The receptacle may include a lid or any other device to close and/or seal the receptacle 610 once full including any of the closing and/or sealing means disclosed herein.

It should be recognized that a container of this invention may include any combination of design and construction features set forth in FIGS. 1A-6C.

Molded Burnable Containers

Figure 7A:
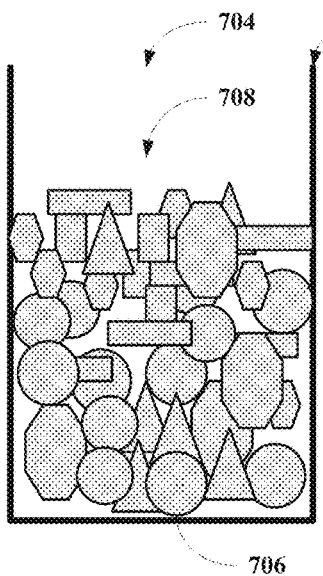
FIGS. 7A-N depict pictorially embodiments of methods to form a molded container.
Figure 7B:
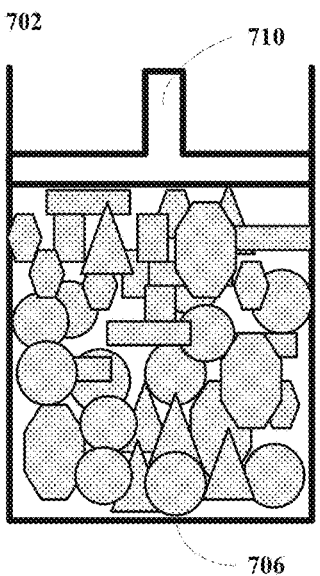
Figure 7C:
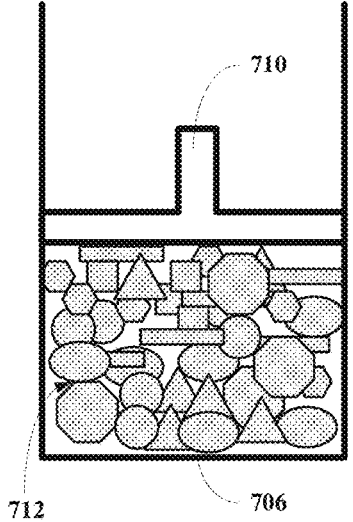
Figure 7D:
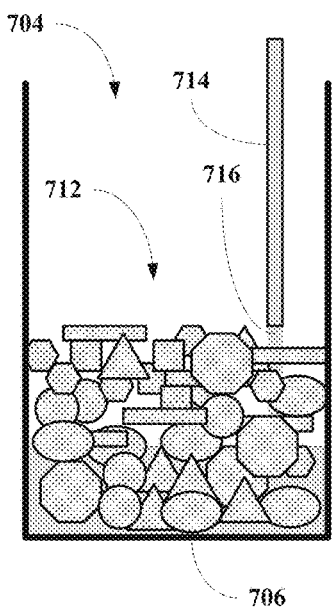
Figure 7E:
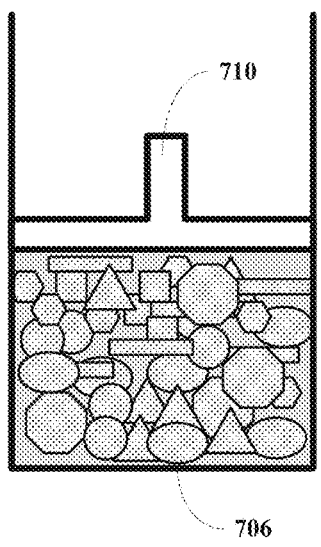
Figure 7F:
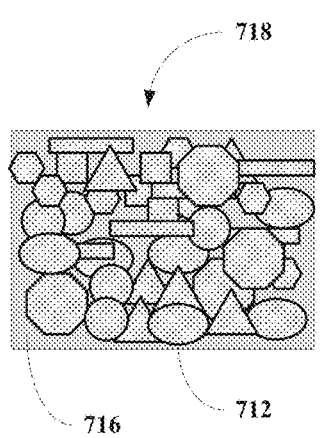
Figure 7G:
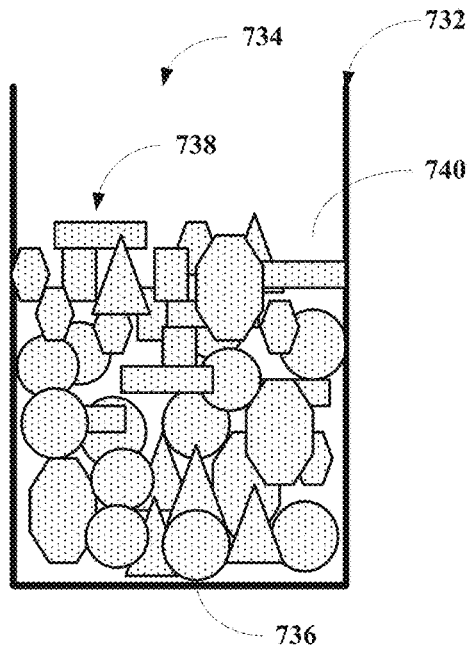
Figure 7H:
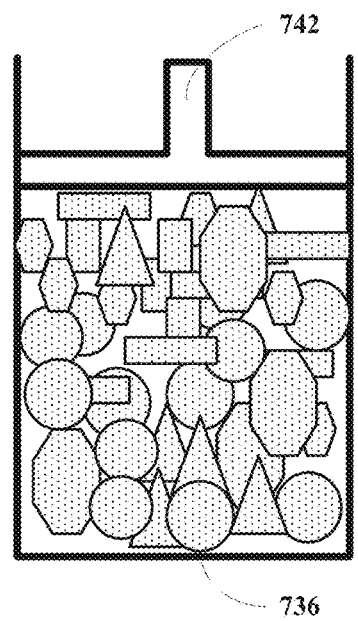
Figure 7I:
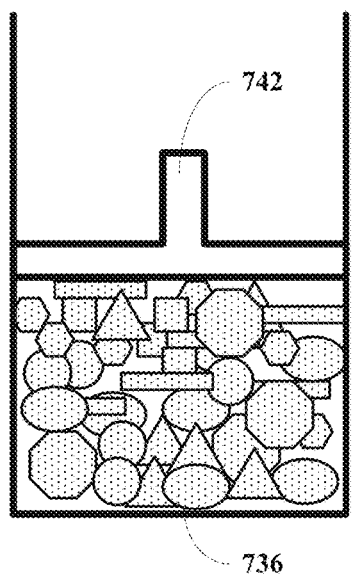

Referring now to FIGS. 7A-F, an embodiment of a method for preparing a molded container of this invention is shown pictorially. Looking at FIG. 7A, a mold 702 is shown to include an opened top 704 and a closed bottom 706. Into the mold 702, source materials 708 comprising a single source material or a plurality of source materials in a plurality of shapes and sizes are deposited—the mold 702 is filled with the source materials. Looking at FIG. 7B, a piston 710 is inserted into the mold opened top 704 to rest on top of the source material 708. Looking at FIG. 7C, the piston 710 is pushed downward compressing the source material 708 to form a compressed source material 712. The piston 710 is then withdrawn and optionally an injector 714 is inserted into the mold 702 through the opened top 704 for injecting a matrix material 716 into the mold 702 to fill in and surround the source material 712 as shown in FIG. 7D. The piston 710 is then reinserted into the mold 702 and the matrix material 716 is thermally cured as shown in FIG. 7E to produce a molded burnable container 718, where the compressed source material 712 is encased in the matrix material 716 as shown in FIG. 7F. In the embodiment, where no matrix material 716 is injected into the mold 702, the compress is sufficient to form a molded container. The mold 702 may be heated to melt any meltable components such as polymers in the source materials so that the compressed materials self adhere.

Figure 7J:
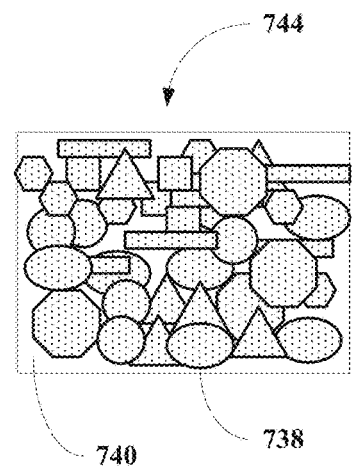

Referring now to FIGS. 7G-J, another embodiment of a method for preparing a molded container of this invention is shown pictorially. Looking at FIG. 7G, a mold 732 is shown to include an opened top 734 and a closed bottom 736. Into the mold 732, source materials 738 comprising a single source material or a plurality of source materials in a plurality of sizes and shapes are deposited and a binding agent or a plurality of binding agents 740—the mold 732 is filled with a source material or mixtures of source materials and a binding agent or a plurality of binding agents. Looking at FIG. 7H, a piston 742 is inserted into the mold opened top 734. Looking at FIG. 7I, the piston 742 is the pushed downward compressing the source materials 738 and the binding agents 740 to form a molded container 744 as shown in FIG. 7J. The mold 732 may be heated to cure the binding agents and/or to melt any polymers in the source materials to assist in the action of the binding agents to bind the compressed materials together.

Referring now to FIGS. 7K-N, another embodiment of a method for preparing a molded container of this invention is shown pictorially. Looking at FIG. 7K, a mold 762 is shown to include an opened top 764, a closed bottom 766 and an injector conduit 768 for optionally injecting a matrix material into the mold during compression described below. Into the mold 762, source materials 770 comprising a single source material or a plurality of source materials in a plurality of sizes and shapes are deposited—the mold 762 is filled with a source material or mixtures of source materials. Looking at FIG. 7L, a piston 772 is inserted into the mold opened top 764 to rest on top of the source material 770. In this embodiment, a matrix material 774 is injected into the mold 762 through the conduit 768. Looking at FIG. 7M, the piston 772 has compressed the source material 770 and optionally the matrix material 774 to form a compression molded form 776 as shown in FIG. 7N to produce a molded burnable container 778. The mold 762 may be heated to melt any polymers in the source materials or to increase thermal curing or setting of the optional matrix material so that the compressed materials adhere or the form cures.

Coating of Sealed Containers

Figure 8A:
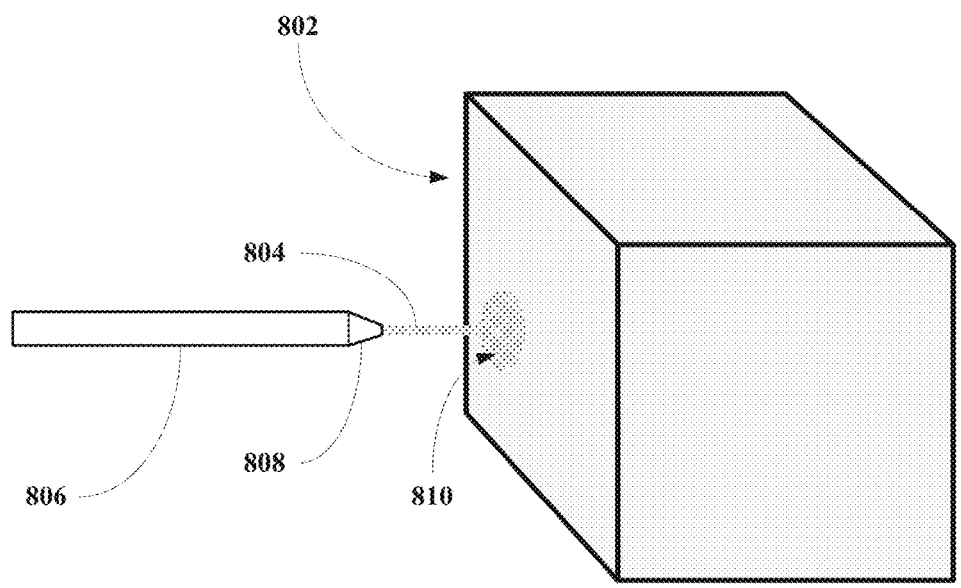
FIGS. 8A-B depict the steps of coating a container with an external coating.
Figure 8B:
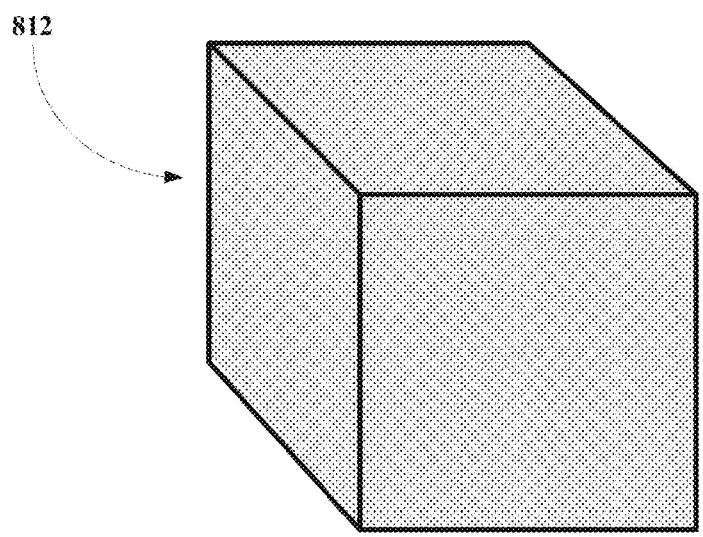
Figure 9A:
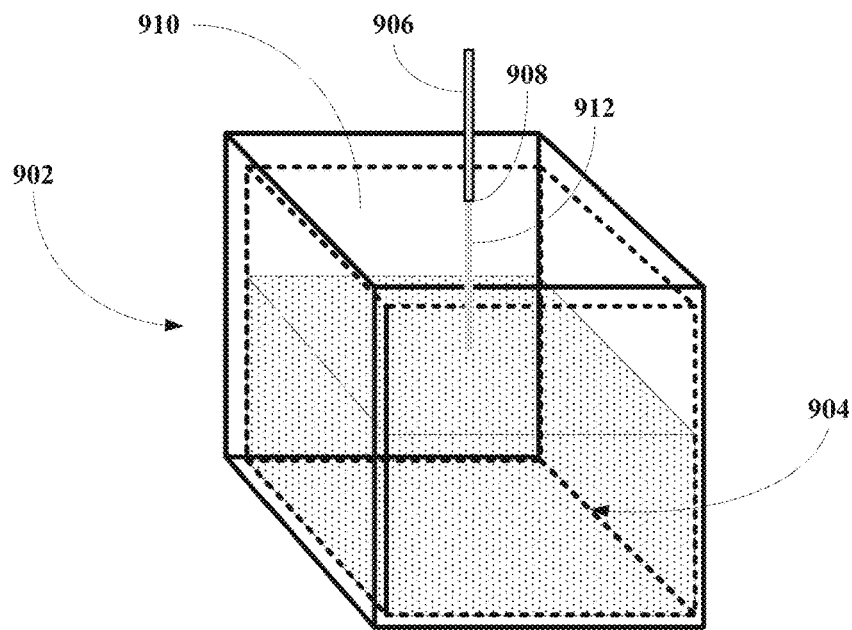
FIGS. 9A-B depict the steps of injecting a filling composition into a filled container.
Figure 9B:
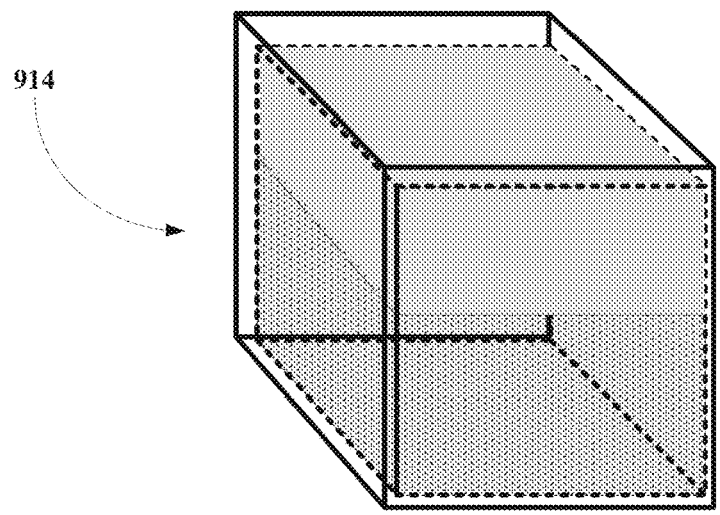

Referring now to FIGS. 8A&B, an embodiment of a method for coating a filled and sealed container of this invention is shown pictorially. Looking at FIG. 8A, a sealed and filled container 802 is coated with a coating material 804 shown here being sprayed onto the container 802 by a sprayer 806 having a nozzle 808. As the coating material 804 exits the nozzle 808, the container 802 is coated in a spray pattern 810. Once coating is complete, a coated container 812 is formed as shown in FIG. 8B. The coating material 804 may be any coating material such as a wax, a polymer material, a thermally curable polymer material, a photo-curable polymer material, an oil, other coatings or mixtures or combination thereof.

Injection Augmented Filled Containers

Referring now to FIGS. 9A-D, an embodiment of a method for injecting an augmenting material into the interior of a filled container is pictorially illustrated. Looking at FIG. 9A, a sealed and filled container 902 filled with a source material 904 is shown with an injector 906 with its distal end 908 inserted into an interior 910 of the container 902. A filling material 912 is then injected into the container 902. The filling material 912 fills the vacant spaces within the filled container 902 to form a filling material augmented filled container 914. The filling material 912 may be a fuel, a polymer, a thermally curable polymer, a photo-curable polymer, a foam, a pro-oxidant, any other material, or mixture or combinations thereof.

Photos of Boxes

Figure 10:
FIG. 10 depict photos of receptacles for use in the containers of this invention.

Referring now to FIG. 10, an embodiment of a set of engineered containers for collecting source materials for disposal.

Figure 11:
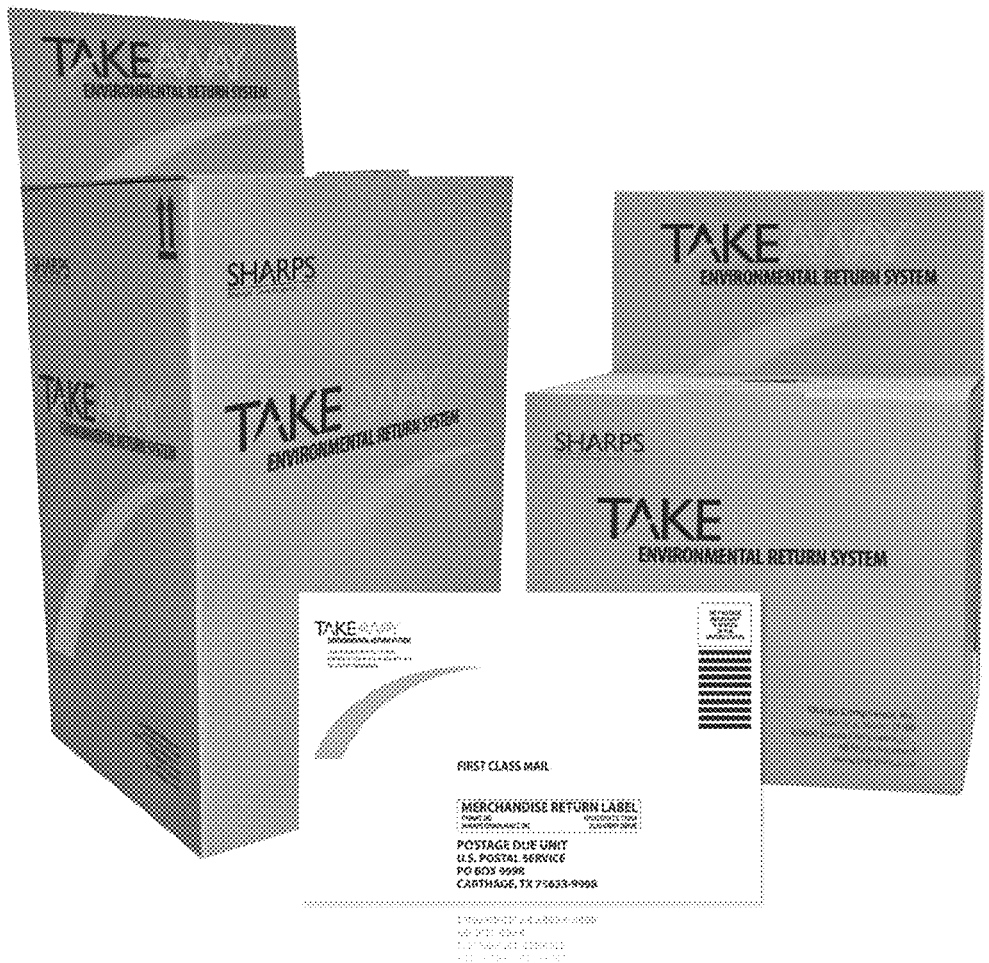
FIG. 11 depict photos of specific embodiments of containers of this invention.

Referring now to FIG. 11, another embodiment of a set of engineered containers for collecting source materials for disposal.

Materials and Combustion Properties

The containers of this invention may be constructed of a variety of different materials or mixtures or combinations of different materials to engineer combustion and post-composition ash composition properties. These construction materials have different combustion properties. Thus, by a proper selection of materials and by a proper design of the container, the combustion post-composition ash composition properties of the container as well as the materials contained there in may be adjusted, altered, modified, and/or augmented. Table I includes a list of various construction materials and their combustion properties:

TABLE I

Materials and Additives and Their Associated Combustion Properties

| Material | Fuel Value (BTU/lb) | Material | Fuel Value (BTU/lb) |
|---|---|---|---|
| paper | 7,200 | polystyrene | 17,800 |
| cardboard | 7,000 | rubber | 13,450 |
| Premium wood pellets | 6,800 | nylon | 13,625 |
| Seasoned firewood | 7,650 | PET | 10,250 |
| Oven dried switch grass | 7,200 | Textiles | 6,900 |
| Shelled corn @15% MC | 5,607 | Fuel oil #2 | 19,154 |
| polyethylene (HDPE) | 19,000 | Fuel oil #6 | 20,519 |
| polyethylene (LLDPE/LLDPE) | 12,050 | Bituminous coal | 13,000 |
| polypropylene | 19,000 | | |

TABLE II

Caloric Values of Various Materials

| | Fuel Value | | |
|---|---|---|---|
| Material | kcal/kg | MJ/kg | kW/kg |
| Bamboo | 3,800 | 15.9 | 4.4 |
| Braun coal | 4,500 | 18.9 | 5.2 |
| Cacao shrub | 3,300 | 13.8 | 3.8 |
| Cardboard | 3,800 | 16.9 | 4.4 |
| Cardboard corrugated | 3,910 | 16.4 | 4.5 |
| Citrus peels | 4,500 | 18.9 | 5.2 |
| China grass | 4,030 | 16.9 | 4.6 |
| Car tires | 8,300 | 34.8 | 9.6 |
| Coconut shell | 3,800 | 15.9 | 4.4 |
| Coffee bean shells | 6,000 | 25.1 | 6.8 |
| Compost | 4,200 | 17.6 | 4.8 |
| Cork | 6,300 | 26.4 | 7.3 |
| Corn | 4,400 | 18.4 | 5.1 |
| Cotton seeds | 3,300 | 13.8 | 3.8 |
| Hay | 3,200 | 13.4 | 3.7 |
| Household waste pre-sorted | 4,500 | 18.9 | 5.2 |
| Hospital waste | 6,780 | 28.5 | 7.8 |
| Leather | 4,020 | 16.8 | 4.6 |
| Manure (dried) | 3,760 | 15.9 | 4.4 |
| Neoprene | 7,100 | 29.7 | 8.2 |
| Nylon | 7,570 | 31.7 | 8.8 |
| Oil sludge | 8,800 | 36.8 | 10.2 |
| Paper | 4,400 | 18.4 | 5.1 |
| Paper sludge | 3,910 | 16.4 | 4.5 |
| Paper coated | 6,390 | 26.8 | 7.4 |
| Paper adhesive coated | 4,200 | 17.6 | 4.8 |
| Newspaper | 3,910 | 16.4 | 4.5 |
| Tar paper | 6,390 | 26.8 | 7.4 |
| Paraffin | 10,340 | 43.3 | 12.1 |
| Polyurethan foam | 9,770 | 40.9 | 11.3 |
| Polyethylene | 10,990 | 46.1 | 12.7 |
| Polypropylene | 11,030 | 46.2 | 12.8 |
| Polystyrol EPS | 9,800 | 41.1 | 11.3 |
| Polystyrol carbon reinforced | 10,840 | 45.4 | 12.6 |
| Rice pods | 2,900 | 12.1 | 3.3 |
| Rubber | 5,600 | 23.4 | 6.5 |
| Sewage sludge (dried) | 3,300 | 13.8 | 3.8 |
| Sunflower residue | 4,200 | 17.6 | 4.8 |
| Straw | 4,000 | 17.2 | 4.6 |
| Tobacco powder | 3,000 | 12.6 | 3.4 |
| Tar and refinery residues | 9,200 | 38.5 | 10.7 |
| Tar acid | 5,600 | 23.4 | 6.5 |
| Textiles | 4,000 | 16.7 | 4.6 |
| Treated wood | 4,500 | 18.9 | 5.2 |
| Untreated wood | 4,200 | 17.6 | 4.8 |
| Plywood | 4,500 | 18.9 | 5.2 |
| Acacia wood | 6,600 | 27.65 | 7.4 |
| Cacao shrub | 3,300 | 13.8 | 3.8 |
| Coconut shells | 3,800 | 15.9 | 4.4 |

TABLE II-continued

Caloric Values of Various Materials

| | Fuel Value | | |
| --- | --- | --- | --- |
| Material | kcal/kg | MJ/kg | kW/kg |
| Coffee bean pods | 6,000 | 25.1 | 6.8 |
| China grass | 4,030 | 16.9 | 4.6 |
| Compost | 4,200 | 17.6 | 4.8 |
| Cork | 6,300 | 26.4 | 7.3 |
| Corn | 4,400 | 18.4 | 5.1 |
| Cotton seeds | 3,300 | 13.8 | 3.8 |
| Eucalyptus wood | 7,200 | 30.1 | 8.2 |
| Hay | 3,200 | 13.4 | 3.7 |
| Manure (dried) | 3,760 | 15.9 | 4.4 |
| Olive oil press residues | 7,400 | 31.0 | 8.4 |
| Pine cones | 7,900 | 33.1 | 9 |
| Reeds | 4,030 | 16.9 | 4.6 |
| Rice pods | 2,900 | 12.1 | 3.3 |
| Sewage sludge (dried) | 3,300 | 13.8 | 3.8 |
| Straw | 4,000 | 17.2 | 4.6 |
| Sunflower residue | 4,200 | 17.6 | 4.8 |
| Tobacco powder | 3,000 | 12.6 | 3.4 |
| Untreated wood | 4,200 | 17.6 | 4.8 |

TABLE III

Physical and Chemical Properties of Containerized Pharmaceuticals for Repurposing

| | Sample | | |
| --- | --- | --- | --- |
| Property (units) | TA2 | TA7 | TA58 |
| Heat Content (BTUs/lb) | 11700 | 11700 | 16800 |
| Ash (% wt) | 19.3 | 7.06 | 5.95 |
| Moisture (% wt) | 4.9 | 10.7 | 5.6 |
| Sulfur (mg/kg) | 1160 | 1230 | 5120 |
| Iron (mg/kg) | 6490 | 329 | 3380 |
| Aluminum (mg/kg) | 6180 | 7440 | 9770 |
| Calcium (mg/kg) | 5790 | 10300 | 22500 |
| Arsenic (mg/kg) | 1.42 | <0.28 | <0.251 |
| Barium (mg/kg) | 11.7 | 12.4 | 5.24 |
| Cadmium (mg/kg) | <0.131 | <0.14 | <0.125 |
| Chromium (mg/kg) | 98.3 | 20.4 | 24 |
| Lead (mg/kg) | 1.09 | 0.834 | 0.4 |
| Selenium (mg/kg) | 1.01 | <0.28 | 1.08 |
| Silver (mg/kg) | 0.202 | <0.14 | <0.125 |
| Mercury (mg/kg) | 0.332 | 0.056 | 0.0257 |
| Chloride (mg/kg) | 6030 | 2560 | 5550 |

TABLE IV

Analytical Results from Packaging Components

| Product | Total Solids | Lead (mg/kg) | Mercury (mg/kg) |
| --- | --- | --- | --- |
| Green Plastic tie | 100% | 4.18 | <0.0099 |
| Red Twist Tie | 100% | 9.55 | <0.010 |
| 15 × 20 4 mil Bag | 100% | <0.971 | 0.0105 |
| 1 Qt Red Plastic Container | 100% | <0.813 | <0.010 |
| Liner Box Brown | 93.0% | <1.05 | 0.0251 |
| 1 Gallon Sharps Container | 100% | <0.990 | <0.0102 |
| White Box-outer | 94.3% | <1.05 | 0.0265 |
| 18 Gallon Lid | 100% | <0.990 | <0.0099 |
| Plastic Lids | 100% | <0.990 | <0.0102 |
| 18 Gallon Container | 100% | <0.952 | <0.0102 |
| 6.5 Bucket | 100% | <0.980 | <0.010 |
| 6.5 Lid | 99.8% | <0.954 | <0.0102 |
| 6.5 Inner Lid | 100% | <0.990 | <0.010 |

TABLE V

Analytical Sample Preparation of Lead and Mercury Determination

| Product | Solid/Organic Metals Digestion | Solid Metals Digestion Hg |
| --- | --- | --- |
| Green Plastic tie | 50/1.01 grams | 50/1.01 grams |
| Red Twist Tie | 50/1.05 grams | 50/1.00 grams |
| 15 × 20 4 mil Bag | 50/1.03 grams | 50/0.98 grams |
| 1 Qt Red Plastic Container | 50/1.23 grams | 50/1.00 grams |
| Liner Box Brown | 50/1.02 grams | 50/0.99 grams |
| 1 Gallon Sharps Container | 50/1.01 grams | 50/0.98 grams |
| White Box-outer | 50/1.01 grams | 50/0.98 grams |
| 18 Gallon Lid | 50/1.01 grams | 50/1.01 grams |
| Plastic Lids | 50/1.01 grams | 50/0.98 grams |
| 18 Gallon Container | 50/1.05 grams | 50/0.98 grams |
| 6.5 Bucket | 50/1.02 grams | 50/1.00 grams |
| 6.5 Lid | 50/1.05 grams | 50/0.98 grams |
| 6.5 Inner Lid | 50/1.01 grams | 50/1.00 grams |

From the data presented above, combustion properties of containers of this invention may be engineered to fuel values between about 6,000 BTU/lb to 20,000 BTU/lb. While the containers may be engineered to have desired fuel values by increasing the amount of high BTU/lb compounds such as polymers, the overall fuel value in BTU/lb of a filled container may be modified by adding into the container high BTU/lb compounds. Thus, the filled containers may have liquid fuels, liquid polymers, powdered polymers, powdered fuels, or mixtures thereof added to the filled containers to increase the fuel value of the filled containers. Additionally, for container designed that have pockets or slots, inserts may be added of high BTU/lb compounds to increase the fuel value of the container. For containers that are coated, the coating may be engineered to improve or retard combustion so that the container starts combusting at an engineered temperatures. The post-combustion ash composition of the container or filled containers may also be altered by added metals or metal oxides to the pockets or slots in the container or added to the interior of the container. By a judicious selection of container construction materials, source material makeup, fill component selection, and container shape and size, the fuel and post-combustion properties of filled and unfilled containers may be altered, modified, and/or augmented. In certain, embodiments, the fuel and post-combustion properties of filled and unfilled containers may be maximized.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method comprising the steps of:
   supplying an engineered burnable container comprising:
   an interior,
   a top,
   a bottom,
   at least one sidewall, and
   at least one opening disposed in the top for depositing a source material into the interior of the container,
   wherein the engineered burnable container has specific container combustion properties and container post-combustion ash properties including at least a container fuel value between 6,000 BTU/lb and 20,000 BTU/lb, a container burn rate, a post-combustion ash composition including post-combustion metal oxide concentrations or mixtures thereof and wherein the container is constructed out of cardboard, a polymer material, a plastic reinforced cardboard, a coated cardboard, or mixtures and combinations thereof, delivering or placing the engineered burnable container or a plurality of the engineered burnable containers to or at a location or locations, wherein a source material is generated or a plurality of source materials are generated, filling the interior of each of the containers with the source material or the source materials to form a filled container or filled containers, retrieving the filled container or the filled containers from the location or the locations, transporting the filled container or the filled containers to a processing facility comprising a power plant, a cement plant or a cement kiln, burning the filled container or the filled containers including the engineered burnable container and the source material contained therein as a fuel to generate heat and an ash composition, and if the processing facility is a power plant, then converting a portion of generated heat into a usable form of energy and wherein the filled containers have minimal ash production, or if the processing facility is a cement kiln or cement plant, converting the ash composition into a clinker or cement composition, wherein the source material or the source materials have combustion properties and post-combustion ash properties, wherein each filled container has specific combustion properties and post-combustion ash properties including at least a filled container fuel value, a filled container burn rate, and a filled container resulting ash composition, which have been adjusted, altered, modified, and/or augmented by the engineered burnable container combustion properties and/or the engineered burnable container post-combustion ash properties.

2. The method 1, further comprising the steps of:
post-processing the filled container or the filled containers to alter combustion properties and post-combustion ash properties of the filled containers.

3. The method of claim 2, wherein the post-processing step comprises:
coating the filled container or the filled containers with a coating selected from the group consisting of a water proof coating, a water resistant coating, a solvent resistant coating, a hermetic sealing coating, a gas tight coating, a gas barrier coating, a puncture resistant coating, or a combination of these coatings.

4. The method of claim 2, wherein the post-processing step comprises:
adding components or fillers to the filled container or the filled containers to alter combustion properties and post-combustion ash properties of the filled container or the filled containers.

5. The method of claim 1, wherein, in the supplying step, the container has a shape selected from the group consisting of a rectangular solid, a spherical solid, an ellipsoidal solid, a cylindrical solid, a toroidal solid, and other solid geometrical shape.

6. The method of claim 1, wherein, in the supplying, the container further comprises:
an exterior coating selected from the group consisting of a water proof coating, a water resistant coating, a solvent resistant coating, a hermetic sealing coating, a gas tight coating, a gas barrier coating, a puncture resistant coating, and a combination of these coatings.

7. The method of claim 1, wherein, in the supplying step, the top, bottom and at least one side wall of the container comprises a multi-layered construction of material to alter the combustion or post-combustion ash properties of the container.

8. The method of claim 1, wherein, in the supplying step, the container further comprises:
a slot or plurality of pockets, where the slot is adapted to be filled with a compound or the pockets are adapted to be filled with a plurality of compounds to alter the combustion and post-combustion ash properties of the container.

9. The method of claim 1, wherein, in the supplying step, the container further comprises:
a lid for sealing the container and closing access to the at least one opening, where the lid fits onto the top.

10. The method of claim 9, wherein, in the supplying step, the lid includes adhesive region so that the lid bonds or seals to the top and/or the at least one sidewall of the container.

11. The method of claim 1, wherein, in the supplying step, the container further comprises:
a closing member associated with the top for closing the opening once the container has been filled with a source material or a plurality of source materials.

12. The method of claim 1, wherein, in the supplying step, the container further comprises:
a liner disposed within an interior of the container.

13. The method of claim 1, wherein, in the supplying step, the container further comprises:
a receptacle including an opening disposed within an interior of the container so that the container opening and the receptacle opening are aligned.

* * * * *